United States Patent
Buseman-Williams et al.

(10) Patent No.: US 7,309,482 B2
(45) Date of Patent: Dec. 18, 2007

(54) LONG LASTING WATERPROOF SUNSCREEN COMPRISING METAL OXIDE AND PEPTIDE CONDITIONER

(75) Inventors: Janine Buseman-Williams, Greenville, DE (US); Xueying Huang, Hockessin, DE (US); Hong Wang, Kennett Square, PA (US); Gary Ken Whiting, North East, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 36 days.

(21) Appl. No.: 11/069,858

(22) Filed: Feb. 28, 2005

(65) Prior Publication Data
US 2005/0249682 A1 Nov. 10, 2005

Related U.S. Application Data

(63) Continuation-in-part of application No. 10/935,642, filed on Sep. 7, 2004, now Pat. No. 7,220,405.

(60) Provisional application No. 60/501,498, filed on Sep. 8, 2003.

(51) Int. Cl.
*A61K 8/02* (2006.01)
*A61K 8/29* (2006.01)
*A61K 8/64* (2006.01)
*A61K 38/02* (2006.01)

(52) U.S. Cl. ............... 424/59; 424/70.9; 424/401; 514/6; 977/836; 977/926

(58) Field of Classification Search ............ 977/926
See application file for complete search history.

(56) References Cited

U.S. PATENT DOCUMENTS

| | | | |
|---|---|---|---|
| 4,683,195 A | 7/1987 | Mullis et al. | |
| 4,800,159 A | 1/1989 | Mullis et al. | |
| 5,223,409 A | 6/1993 | Ladner et al. | |
| 5,403,484 A | 4/1995 | Ladner et al. | |
| 5,449,754 A | 9/1995 | Nishioka | |
| 5,451,390 A | 9/1995 | Hartmann et al. | |
| 5,480,971 A | 1/1996 | Houghten et al. | |
| 5,510,120 A * | 4/1996 | Jones et al. | 424/499 |
| 5,571,698 A | 11/1996 | Ladner et al. | |
| 5,585,275 A | 12/1996 | Hudson et al. | |
| 5,639,603 A | 6/1997 | Dower et al. | |
| 5,672,330 A | 9/1997 | Hartmann et al. | |
| 5,698,205 A * | 12/1997 | Bruckner et al. | 424/401 |
| 5,762,914 A | 6/1998 | Hartmann et al. | |
| 5,788,973 A | 8/1998 | Ascione | |
| 5,837,500 A | 11/1998 | Ladner et al. | |
| 6,958,148 B1 * | 10/2005 | Green et al. | 424/94.5 |
| 2003/0152976 A1 | 8/2003 | Janssen et al. | |
| 2004/0191285 A1 | 9/2004 | Bassi et al. | |
| 2005/0129634 A1 * | 6/2005 | Frerichs et al. | 424/59 |
| 2007/0112174 A1 * | 5/2007 | Shiba et al. | 530/329 |

FOREIGN PATENT DOCUMENTS

| | | |
|---|---|---|
| EP | 0 546 049 B1 | 6/1993 |
| WO | WO 93/24631 A1 | 12/1993 |
| WO | WO 2004/048399 A2 | 6/2004 |

OTHER PUBLICATIONS

U.S. Appl. No. 60/434,158, filed Dec. 17, 2002, Stephan De La Veaux et al.
U.S. Appl. No. 10/935,642, filed Sep. 7, 2004, Xueying Huang et al.
U.S. Appl. No. 11/011,670, filed Dec. 14, 2004, Frerichs et al.
U.S. Appl. No. 10/737,357, filed Dec. 16, 2003, Frerichs et al.
D.J. Kemp, Direct Immunoassay for Detecting *Escherichia coli* Colonies That Contain Polypeptides Encoded by Cloned DNA Segments, Proc. Natl. Acad. Sci. USA, 1981, pp. 4520-4524, vol. 78.
Helfman et. al., Identification of Clones That Encode Chicken Tropomyosin by Direct Immunological Screening of s CDNA Expression Library, Proc. Natl. Acad. Sci. USA, 1983, pp. 31-35, vol. 80.
Chien et. al., The Two-Hybrid System: a Method to Identify and Clone Genes for Proteins That Interact With a Protein of Interest, Proc. Natl. Acad. Sci. USA, 1991, pp. 9578-9582, vol. 88 (21).
M. Dani, Biological Libraries, J. of Receptor & Signal Transduction Res., 2001, pp. 447-468, vol. 21 (4).
Sidhu et. al., Phage Display for Selection of Novel Binding Peptides, Methods in Enzymology, 2000, pp. 333-363, vol. 328.

* cited by examiner

*Primary Examiner*—Jeffrey Edwin Russel

(57) ABSTRACT

The disclosure provides a sunscreen formulation comprising a peptide-based metal oxide sunscreen agent, such as titanium dioxide nanoparticles, and a fluid vehicle.

30 Claims, No Drawings

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Skin-binding peptide

```
<400> SEQUENCE: 1

Thr Pro Phe His Ser Pro Glu Asn Ala Pro Gly Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 2

Phe Thr Gln Ser Leu Pro Arg
1               5

<210> SEQ ID NO 3
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 3

Lys Gln Ala Thr Phe Pro Pro Asn Pro Thr Ala Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 4

His Gly His Met Val Ser Thr Ser Gln Leu Ser Ile
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 5

Leu Ser Pro Ser Arg Met Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 6

Leu Pro Ile Pro Arg Met Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Skin-binding peptide
```

```
<400> SEQUENCE: 7

His Gln Arg Pro Tyr Leu Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 8

Phe Pro Pro Leu Leu Arg Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 9

Leu Glu Ser Gly Asp Glu Val Asp
1               5
```

LONG LASTING WATERPROOF SUNSCREEN COMPRISING METAL OXIDE AND PEPTIDE CONDITIONER

CROSS-REFERENCE TO RELATED APPLICATIONS

This application is a continuation-in-part of application Ser. No. 10/935,642 filed on Sep. 7, 2004, now U.S. Pat. No. 7,220,405, which claims the benefit of U.S. Provisional Application 60/501,498, filed on Sep. 8, 2003, now expired, application Ser. No. 10/935,642 is incorporated herein by reference in its entirety.

This application is a continuation-in-part of application Ser. No. 10/935,642 filed on Sep. 7, 2004 which is incorporated herein by reference in its entirety.

FIELD OF THE INVENTION

The present invention relates to sunscreen compositions. More specifically, the invention relates to sunscreen screen compositions based upon inorganic metal oxides and skin-binding, peptides.

BACKGROUND OF THE INVENTION

Certain metal oxides, such as titanium dioxide and zinc oxide, are known for their sunscreen properties. Titanium dioxide has low toxicity and is non-irritating to the skin.

Nanostructured particles and materials are currently attracting considerable attention. The small size of nanoparticles (generally used to indicate particles less than 100 nm), which can be responsible for the different properties (electronic, optical, electrical, magnetic, chemical, and mechanical) of nanoparticles and nanostructured materials with respect to the bulk material, makes them suitable for new industrial applications. In many of these new applications, it is imperative to provide and maintain the particles and materials well dispersed in a fluid medium, such as water, organic solvent, wax, oil, polymer or mixtures of these.

Titanium dioxide (TiO2) nanoparticles are substantially transparent to visible light, that is, are transparent, but reflect, scatter and absorb ultraviolet light. The nanoparticles, in contrast to pigment-sized titanium dioxide particles, can be beneficial in sunscreen formulations where transparency of the formulation is desirable.

A major problem with current skin care compositions is that they lack the required durability for long-lasting effects. For this reason, there have been attempts to enhance the binding of the skin care agent to the skin.

A need exists for sunscreen formulations that provide improved durability for long lasting effects.

SUMMARY OF THE INVENTION

In a first embodiment of the invention, the disclosure provides a sunscreen formulation comprising:
(a) a peptide-based metal oxide sunscreen agent, and
(b) a fluid vehicle.

The peptide-based skin conditioner may be a diblock composition having the general structure $(SBP)_n$-SSA, wherein SBP is a skin-binding peptide, SSA is a metal oxide sunscreen agent and n ranges from 1 to about 50, specifically n ranges from about 1 to about 10.

In one embodiment of the invention, the peptide-based metal oxide sunscreen agent may be a triblock composition having the general structure $[(SBP)_m\text{-}S]_n$-SSA, wherein SBP is a skin-binding peptide; S is a spacer having first and second ends; SSA is a metal oxide sunscreen agent; m ranges from 1 to about 50; and n ranges from 1 to about 500, specifically n ranges from about 1 to about 10.

In one embodiment of the invention, the metal oxide sunscreen agent comprises at least one metal oxide selected from the group consisting of titanium dioxide, zinc oxide, cerium oxide and iron oxide, more typically from the group of titanium dioxide and zinc oxide, and still more typically titanium dioxide. The metal oxide can be in the pigment size range or in the nanoparticle size range.

The metal oxide sunscreen agent can be prepared by a process comprising:
(a) forming a slurry of metal oxide;
(b) contacting the slurry of metal oxide with a densifying agent;
(c) contacting the slurry with a source of a metal oxide selected from the group consisting of a source of alumina, a source of silica or both to form a treated metal oxide; and
(d) recovering the treated metal oxide formed in step (c).

Typically, the metal oxide prepared by this process is titanium dioxide, especially titanium dioxide nanoparticles. The metal oxide particles prepared by this process have been found to have a high photo stability and/or high chemical stability. In addition the nanoparticles have a reduced tendency to form agglomerates when formulated into sunscreen composition.

The metal oxide nanoparticles may be prepared by any processes which are well known in the art including but not limited to plasma processes or a sol gel process.

In a second embodiment, the invention provides a process for preparing a sunscreen formulation comprising mixing a peptide-based metal oxide sunscreen agent and a fluid vehicle.

BRIEF DESCRIPTION OF THE FIGURES AND SEQUENCE DESCRIPTIONS

The invention can be more fully understood from the following detailed description, and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-8 are the amino acid sequence of skin-binding peptides.

SEQ ID NO: 9 is the amino acid sequence of the Caspase 3 cleavage site.

DETAILED DESCRIPTION OF THE INVENTION

The present disclosure provides a sunscreen formulation that is long-lasting and durable, water resistant and that has a soft feel on the skin. Improved water resistance eliminates the need for reapplication after exposure of the skin to water. The improved formulation may be provided as a light spray-on system free of heavy waxes and oils commonly used to impart water resistance.

The sunscreen formulation of this disclosure comprises:
(a) a peptide-based metal oxide sunscreen agent, and
(b) a fluid vehicle.

Metal Oxide Sunscreen Agent:

The metal oxide sunscreen agent may be any metal oxide having sunscreen properties. Typically such metal oxides are selected from the group consisting of titanium dioxide, zinc oxide, cerium oxide and iron oxide, more typically from the group of titanium dioxide and zinc oxide, and still more typically titanium dioxide. Pigment-sized metal oxide particles such as titanium dioxide having a particle size greater than 100 nm in diameter can be particularly useful when an opaque sunscreen formulation is preferred. Particle size diameter is determined by measuring the primary particles.

Metal oxide nanoparticles, particularly titanium dioxide nanoparticles can be used especially when translucency of the sunscreen formulation is preferred. Specific examples of nanoparticle metal oxides are selected from the group of titanium dioxide, zinc oxide, cerium oxide and iron oxide, more typically from the group of titanium dioxide and zinc oxide, and still more typically titanium dioxide. Nanoparticles typically have a particle size that is less than 100 nm in diameter. Particle size diameter is determined by measuring the diameter of the primary particles.

In one embodiment of the invention the metal oxide particles can be treated with at least one of a source of silica and alumina which can be added to a slurry of the metal oxide particles, water and a densifying agent to form the treated metal oxide.

The present invention provides metal oxide particles which are treated, preferably surface treated, with amorphous alumina in the presence of a densifying agent. More specifically, the particles are coated in a wet treatment process with amorphous alumina in the presence of a densifying agent. Optionally, the particles are further treated, preferably surface treated, with amorphous silica also in the presence of a densifying agent.

The present invention also can provide metal oxide particles which are treated, preferably surface treated, with amorphous silica in the presence of a densifying agent. More specifically, the particles are coated in a wet treatment process with amorphous silica in the presence of a densifying agent. Optionally, the particles are further treated with amorphous alumina also in the presence of a densifying agent.

In one embodiment of this invention, a slurry of the metal oxide particles is heated and densifying agent is added to the slurry. The slurry is an aqueous mixture of the metal oxide particles, which are water insoluble. The slurry is pH adjusted to form a basic composition and then treated with a source of alumina or silica or both, typically sodium aluminate or sodium silicate. After treatment with the source of alumina or silica or both the slurry is held at a certain pH and elevated temperature for a period of time sufficient to cure the particles. An objective of the curing step is to deposit alumina and/or silica onto the particles, more typically, by coating the particles with a layer of alumina and/or silica.

In one embodiment of the invention the initial temperature of the slurry is optimally greater than about 30° C., typically greater than about 35° C., even more typically greater than about 50° C., and yet more typically above about 60° C. Temperatures can range from about 30 to about 100° C., more typically in the range of about 40° C. to about 100° C. and still more typically from about 60° to about 100° C., although lower temperatures might also be effective. In one embodiment of the invention the initial temperature of the slurry is optimally greater than about 50° C., typically above about 60° C., more typically in the range of about 60° to about 100° C., although lower temperatures might also be effective. The amount of the source of alumina and/or silica is optimally in the range of between about 5 and about 15% as $Al_2O_3$ based on weight of untreated metal oxide.

A strong mineral acid can be employed during the alumina and/or silica treatment. Any strong mineral acid, including but not limited to HCl, $HNO_3$, and $H_2SO_4$ could be used. The optimal acid addition time for a small lab scale batch process ranges from 0.5 to about 2.0 minutes per 1% $Al_2O_3$ and/or $SiO_2$ added (up to 30 minutes per 1% $Al_2O_3$ and/or $SiO_2$ for large plant scale batches). Longer times can lead to better product but at the expense of rate.

After adding the alumina and/or silica, the pH of the slurry is typically held at a neutral level. Optimally at 7+0.5. Higher values might lead to undesired phases, particularly for alumina; lower values to incomplete deposition.

The alumina and/or silica treated slurry is then held for a period of time sufficient to deposit alumina and/or silica onto the metal oxide particles typically by forming a coating of alumina and/or silica on the particles. The holding time is typically 3 minutes per 1% alumina and/or silica for small lab scale batches (up to 20 minutes per 1% alumina and/or silica for large plant batches). Shorter times can be used but the treatment may not be as effective. This holding step is typically carried out while maintaining a neutral pH and elevated temperature. Thus the pH usually is maintained at 7.0+0.5. In one embodiment of the invention the temperature of the slurry is optimally greater than about 30° C., typically greater than about 35° C., even more typically greater than about 50° C., and yet more typically above about 60° C. Temperatures can range from about 30 to about 100° C., more typically in the range of about 40° C. to about 100° C. and still more typically from about 60° to about 100° C., although lower temperatures might also be effective. The temperature is usually maintained at about 50° C., typically above about 45° C., more typically at about 55 to about 60° C.

Metal oxide compositions, especially nanoparticle compositions, of the present invention generally include from about 3 to about 20%, more typically from about 5 to about 15% amorphous alumina based on the weight of the untreated metal oxide. Particulate compositions of the present invention generally can include from about 2 to about 20, generally from about 5 to about 18% amorphous silica based on the weight of the untreated metal oxide.

The alumina and/or silica treated metal oxide particles, usually, are then filtered, washed and dried. When nanoparticles are used as the metal oxide, the final particles are in a size range less than pigmentary; typically the average particle size in diameter is between about 80 and about 125 nanometers, sometimes less than about 100 nanometers determined by techniques well known in the art such as scanning electron micrograph.

In a preferred embodiment of this invention the slurry is treated with both a source of silica and a source of alumina. In this embodiment, a slurry of metal oxide particles is heated and densifying agent is added to the slurry. The slurry is an aqueous mixture of the metal oxide particles, which are water insoluble. The slurry is then pH adjusted to form a basic composition and then treated with a source of silica, typically sodium silicate. The pH is decreased to a more neutral level by addition of acid, after which the slurry is treated with a source of alumina, typically sodium aluminate. After treatment with the source of silica and alumina the slurry is held at a certain pH and elevated temperature for a period of time sufficient to cure the particles. An objective of the curing step is to deposit silica and alumina onto the particles, more specifically, by coating the particles with a layer of silica and a layer of alumina.

The treatment occurs in the presence of a densifying agent. The densifying agent is important for densifying the coatings of silica and/or alumina. Suitable densifying agents include citric acid or a source of phosphate ion such as phosphoric acid or a source of sulfate ion such as sodium sulfate. Citric acid is the preferred densifying agent because of its dispersion enhancing properties. A useful amount of densifying agent is an amount sufficient to adequately densify the silica and alumina coatings. An excess of densification agent will maximize densification of the silica and alumina coatings but may lead to waste of the densifying agent.

Suitable amounts of the densifying agent can be in the range of about 0.5% to about 3.0%, more typically from about 0.8% to about 2.4% based on weight of untreated metal oxide. The concentration of metal oxide in the slurry ranges from about 50 g/l to about 500 g/l more typically from about 125 to 250 grams per liter, although lower levels are also possible. Good coating consistency has been found with a relatively low concentration slurry. The temperature of the slurry usually ranges from about 30 to about 100, typically about 35 to about 100, more typically about 45 to about 100° C. optimally from about 85 to about 100° C., although lower or higher temperatures might also be effective. Before adding the source of silica, the slurry is maintained in the alkaline range, typically the pH is above 8.5, more typically 9.0 or higher although this may depend on the equipment used (lower pH may be possible for continuous wet treatment). The optimal silica deposition weight is typically between about 2 and about 20, more typically from about 5 to about 18% as $SiO_2$ based on weight of untreated metal oxide. However, improvements are likely to be seen at any silica level.

Any strong mineral acid, including HCl, $HNO_3$ and $H_2SO_4$ may be used to neutralize the slurry prior to alumina treatment. The optimal acid addition time for batch process ranges from 0.5 to about 4 minutes per 1% $SiO_2$ added for small lab scale batches (up to 30 minutes per 1% $SiO_2$ for large plant scale batches). Longer times can lead to better product at the expense of rate.

The silica treated slurry is then held for a period of time which is preferably sufficient to deposit a coating of silica on the metal oxide particles. The holding time is typically 5 minutes per 1% silica for small lab scale batches (up to 20 minutes per 1% silica for large plant scale batches). Shorter times can be used but the coating may not be as effective. This holding step is typically carried out while maintaining a neutral to alkaline pH and elevated temperature. Thus, the pH usually is maintained at 7.0+1.0 and higher, typically up to and including about 10. The temperature is usually maintained above about 80° C., typically above about 90° C., more typically at about 95 to about 100° C.

In the alumina treatment the initial temperature of the slurry is optimally greater than about 80° C., typically above about 90° C., more typically in the range of about 95° to about 100° C., although lower temperatures might also be effective (or even more effective but at the expense of energy and time necessary to chill the slurry). Aluminate amount is optimally in the range of between about 5 and about 15% as $Al_2O_3$ based on weight of untreated metal oxide.

Any strong mineral acid can be employed during the alumina treatment including HCl, $HNO_{31}$ and $H_2SO_4$. The optimal acid addition time for a small lab scale batch process ranges from 0.5 to about 2.0 minutes per 1% $Al_2O_3$ added (up to 30 minutes per 1% $Al_2O_3$ for large plant scale batches). Longer times can lead to better product at the expense of rate.

After adding the alumina, the pH of the slurry is typically held at a neutral level. Optimally at 7+0.5. Higher values might lead to undesired alumina phase; lower values to incomplete deposition.

The alumina treated slurry is then held for a period of time sufficient to form a coating of alumina on the metal oxide particles to which a silica coating has been deposited. The holding time is typically 3 minutes per 1% alumina for small lab scale batches (up to 20 minutes per 1% alumina for large plant batches). Shorter times can be used but the coating may not be as effective. This holding step is typically carried out while maintaining a neutral pH and elevated temperature. Thus the pH usually is maintained at 7.0+0.5. The temperature is usually maintained at about 50° C., typically above about 45° C., more typically at about 55 to about 60° C.

Silica and alumina treated particulate compositions, especially nanoparticle compositions, of the present invention generally can include from about 2 to about 20, generally from about 5 to about 18% amorphous silica based on the weight of the untreated metal oxide and from about 3 to about 20%, more typically from about 5 to about 15% amorphous alumina based on the weight of the untreated metal oxide.

The silica and alumina treated metal oxide particles, usually, are then filtered, washed and dried. When nanoparticles are used as the metal oxide, the final particles are in a size range less than pigmentary; typically the average particle size in diameter is between about 80 and about 125 nanometers, additionally less than about 100 nanometers.

Titanium dioxide nanoparticles are preferred for use in this invention and for the silica-alumina treatment process described hereinabove. Any titanium dioxide nanoparticles can be suitable. As an example, suitable titanium dioxide nanoparticles are described in U.S. Pat. Nos. 5,451,390; 5,672,330; and 5,762,914. Titanium dioxide P25 is an example of a suitable commercial product available from Degussa. Other commercial suppliers of titanium dioxide nanoparticles include Kemira, Sachtleben and Tayca.

The titanium dioxide nanoparticles typically have an average particle size diameter of less than 100 nanometers (nm) as determined by dynamic light scattering which measures the particle size distribution of particles in liquid suspension. The particles are typically agglomerates which may range from about 3 nm to about 6000 nm. Any process known in the art can be used to prepare such particles. The process may involve vapor phase oxidation of titanium halides or solution precipitation from soluble titanium complexes, provided that titanium dioxide nanoparticles are produced.

A preferred process to prepare titanium dioxide nanoparticles is by injecting oxygen and titanium halide, preferably titanium tetrachloride, into a high-temperature reaction zone, typically ranging from 400 to 2000 degrees centrigrade. Under the high temperature conditions present in the reaction zone, nanoparticles of titanium dioxide are formed having high surface area and a narrow size distribution. The energy source in the reactor may be any heating source such as a plasma torch. Optionally, the reactor may also include a flow homogenizer that ensures that feeds from the reactant inlets enter the reactor chamber downstream of the recirculation zone induced by the high temperature gas discharge.

A flow homogenizer is described in U.S. Provisional Patent Application No. 60/434,158 filed on Dec. 17, 2002 which is incorporated herein by reference in its entirety.

The metal oxide, especially titanium dioxide, can be substantially pure or it may contain one or more other inorganic materials. The crystal lattice of the metal oxide can be doped with an element to impart new or modified properties to the metal oxide. Examples of dopants include silicon, aluminum, zirconium, iron, manganese, vanadium, chromium or magnesium. The crystal lattice may be doped with iron or manganese to change the color of the metal oxide. For example, the crystal lattice of the metal oxide, especially titanium dioxide, can be doped with iron or manganese to impart a "buff" color to the titanium dioxide. Such a colored titanium dioxide can be useful for sunscreen formulations where it is desirable for the formulation to impart a tanned look to the skin. The crystal lattice of the metal oxide, especially titanium dioxide, can also be doped with an element such as manganese, iron, vanadium or chromium to reduce the photoactivity of the titanium dioxide. A commercially available titanium dioxide product which is doped is Hombitec® RM 300 and Hombitec® RM 400 sold by Sachtleben. Oxonica Limited has described an ultrafine titanium dioxide with the inclusion of a small amount (less than 1%) of manganese that product is referred to as Optisol™. The dopant is typically present in a minor amount, typically in the range of about 0.01% to about 5%, specifically about 0.1% to about 1%, based on the entire weight of the metal oxide.

The metal oxide which is optionally treated with silica and/or alumina can contain one or more additional metal oxides. The additional metal oxide can be one or more of silica, alumina, zirconia and magnesia which can be incorporated into the metal oxide particle using techniques known by those skilled in the art. As an example in the case of titanium dioxide these metal oxides can be incorporated when the titanium compounds are co-oxidized or co-precipitated with other metal oxide compounds. If such co-metals are present, they are preferably present in an amount of about 0.1 to about 5% based on the total metal oxide weight. The titanium dioxide may also have one or more such metal oxide coatings applied using techniques known by those skilled in the art prior to any other treatment including the silica-alumina treatment described hereinabove. In one embodiment of the invention, a slurry of substantially pure titanium dioxide is "pretreated" with alumina prior to contacting the slurry with citric acid. The pretreatment is typically to an amount of about 1 to about 4% based on the total metal oxide weight.

Typically, for alumina pretreated titanium dioxide, the final alumina level of products made by the invention is about 2.5% higher if the $TiO_2$ is pretreated with alumina. Benefits have been found when the titanium dioxide nanoparticles containing in a coating or by incorporation into the particle alumina is silica-alumina treated as described hereinabove. For example, it has been found that the silica treatment step is more effective when applied to titanium dioxide particles that contain alumina. In addition, it has been found that the chemical stability (determined by the Vitamin C Yellowing Test which is described below) is higher and fewer oversized particles are produced by the process, specifically about 10% fewer oversized particles, as compared to a titanium dioxide starting material that does not contain alumina. By the term "oversized particles" it is meant agglomerates which are greater in diameter than about 200 nm, as determined by the MICROTRAC ultrafine particle analyzer.

One area of increasing demand for metal oxide sunscreen agents is in personal care formulations, particularly in sunscreens as a sunscreen agent. Titanium dioxide nanoparticles provide protection from the harmful ultraviolet rays of the sun (UV A and UV B radiation). Both UV A and UV B radiation have been implicated in numerous skin problems, ranging from causing freckles, sunburn (erythema), and wrinkles, and premature aging. In addition, UV A radiation has been linked with skin cancer.

A dispersant is usually required to effectively disperse metal oxide, particularly titanium dioxide, nanoparticles in a fluid medium. Careful selection of dispersants is important. Typical dispersants for use with titanium dioxide nanoparticles include aliphatic alcohols, saturated fatty acids and fatty acid amines.

Typically the amount of metal oxide sunscreen agent, particularly titanium dioxide nanoparticles, incorporated into a sunscreen formulation can be up to about 25 wt. %, more typically from about 0.1 wt. % to up to about 15 wt. %, and still more typically about 6 wt. %, based on the weight of the formulation, the amount depending upon the desired sun protection factor (SPF) of the formulation.

Peptide-Based Skin Conditioner:

The following definitions are used herein and should be referred to for interpretation of the claims and the specification.

"SBP" means skin-binding peptide.

"SSA" means metal oxide sunscreen agent.

"S" means spacer.

The term "peptide" refers to two or more amino acids joined to each other by peptide bonds or modified peptide bonds.

The term "skin" as used herein refers to human skin, or pig skin, Vitro-Skin® and Epiderm™ that are substitutes for human skin.

The term "phage-peptide-skin complex" means structure comprising a phage-peptide bound to skin via a binding site on the peptide.

The term "non-target" refers to a substrate for which peptides with a binding affinity thereto are not desired. For the selection of skin care composition-resistant skin-binding peptides, non-targets, include, but are not limited to, hair and plastic.

The term "stringency" as it is applied to the selection of skin-binding, peptides of the invention, refers to the concentration of the eluting agent (usually detergent) used to elute peptides from the skin. Higher concentrations of the eluting agent provide more stringent conditions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |

-continued

| Amino Acid | Three-Letter Abbreviation | One-Letter Abbreviation |
| --- | --- | --- |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences.

"Chimeric gene" refers to any gene that is not a native gene, comprising regulatory and coding sequences that are not found together in nature. Accordingly, a Chimeric gene may comprise regulatory sequences and coding sequences that are derived from different sources, or regulatory sequences and coding sequences derived from the same source, but arranged in a manner different than that found in nature.

A "foreign" gene refers to a gene not normally found in the host organism, but that is introduced into the host organism by gene transfer. Foreign genes can comprise native genes inserted into a non-native organism, or Chimeric genes.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Skin-Binding Peptides:

Skin-binding peptides (SBPs) as defined herein are peptide sequences that specifically bind with high affinity skin. The skin-binding peptides of the invention are from about 7 amino acids to about 45 amino acids, more preferably, from about 7 amino acids to about 20 amino acids, most preferably from about 7 to about 12 amino acids.

Suitable skin-binding sequences may be selected using methods that are well known in the art. The peptides of the present invention are generated randomly and then selected against a specific skin sample based upon their binding affinity for skin. The generation of random libraries of peptides is well known and may be accomplished by a variety of techniques including, bacterial display (kemp, d. j.; *proc. Natl. Acad. Sci. Usa* 78(7):4520-4524 (1981), and helfman et al., *proc. Natl. Acad. Sci.* Usa 80(1):31-35, (1983)), yeast display (chien et al., *proc natl acad sci usa* 88(21):9578-82 (1991)), combinatorial solid phase peptide synthesis (U.S. Pat. Nos. 5,449,754, 5,480,971, 5,585,275, 5,639,603), and phage display technology (U.S. Pat. Nos. 5,223,409, 5,403,484, 5,571,698, 5,837,500). Techniques to generate such biological peptide libraries are well known in the art. Exemplary methods are described in dani, m., *j. Of receptor & signal transduction res.*, 21(4):447-468 (2001), sidhu et al., *methods in enzymology* 328:333-363 (2000), and *phage display of peptides* and *proteins, a laboratory manual*, brian k. Kay, jill winter, and john mccafferty, eds.; academic press, ny, 1996. Additionally, phage display libraries may be purchased from new england biolabs (beverly, Mass.).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

Specifically, after a suitable library of peptides has been generated, the library is contacted with an appropriate amount of skin sample. Human skin samples may be obtained from cadavers or in vitro human skin cultures. Additionally, pig skin, Vitro-Skin® (available from IMS inc., Milford, Conn.) and Epiderm™ (available from Mattek corp., Ashland, Mass.) may be used as substitutes for human skin. The library of peptides is dissolved in a suitable solution for contacting the skin sample. In one embodiment, the library of peptides is dissolved in a buffered aqueous saline solution containing a surfactant. A suitable solution is tris-buffered saline (tbs) with 0.5% tween® 20. The solution may be agitated by any means in order to increase the mass transfer rate of the peptides to the skin surface, thereby shortening the time required to attain maximum binding. The time required to attain maximum binding varies depending on a number of factors, such as size of the skin sample, the concentration of the peptide library, and the agitation rate. The time required can be determined readily, by one skilled in the art, using routine experimentation. Typically, the contact time is 10 minutes to one hour. Optionally, the phage display library may be contacted with a non-target, such as hair or plastic, either prior to or simultaneously with contacting the skin sample to remove the undesired phage-peptides that bind to the non-target.

Upon contact, a number of the randomly generated peptides will bind to the skin to form a peptide-skin complex. Unbound peptide may be removed by washing. After all unbound material is removed, peptides having varying degrees of binding affinities for the test substrate may be fractionated by selected washings in buffers having varying stringencies. Increasing the stringency of the buffer used increases the required strength of the bond between the peptide and substrate in the peptide-substrate complex.

A number of substances may be used to vary the stringency of the buffer solution in peptide selection including, but not limited to, acidic pH (1.5-3.0); basic ph (10-12.5); high salt concentrations such as $MgCl_2$ (3-5 m) and licl (5-10 m); water; ethylene glycol (25-50%); dioxane (5-20%); thiocyanate (1-5 m); guanidine (2-5 m); urea (2-8 m); and various concentrations of different surfactants such as SDS (sodium dodecyl sulfate), DOC (sodium deoxycholate), Nonidet P-40, Triton X-100, Tween® 20, wherein Tween® 20 is more typical. These substances may be prepared in buffer solutions including, but not limited to, tris-HCl, tris-buffered saline, tris-borate, tris-acetic acid, triethylamine, phosphate buffer, and glycine-HC, wherein tris-buffered saline solution is preferred.

It will be appreciated that peptides having increasing binding affinities for skin may be eluted by repeating the selection process using buffers with increasing stringencies.

The phage-peptide-skin complex is then contacted with an eluting agent for a period of time, typically, 1 to 30 minutes, to dissociate the phage-peptide from the skin; however, some of the phage-peptide may still remain bound to the skin after this treatment. Optionally, the phage-peptide-skin complex is transferred to a new container before contacting with the eluting agent. The eluting agent may be any known eluting agent including, but not limited to, acid (ph 1.5-3.0); base (ph 10-12.5); high salt concentrations such as $MgCl_2$ (3-5 m) and LiCl (5-10 m); water; ethylene glycol (25-50%); dioxane (5-20%); thiocyanate (1-5 m); guanidine (2-5 m); and urea (2-8 m), wherein treatment with an acid is more typical. If the elution buffer used is an acid or base, then, a neutralization buffer is added to adjust the ph to the neutral range. Any suitable buffer may be used, wherein 1 m tris-HCl ph 9.2 is preferred for use with an acid elution buffer.

The eluted phage-peptides or the remaining bound phage-peptides, or both the eluted phage-peptides and the remaining bound phage-peptides are then amplified using methods known in the art. For example, the eluted phage-peptides and the remaining bound phage-peptides may be amplified by infecting a bacterial host cell, such as *E. coli* ER2738, as described by Huang et al., supra. The infected host cells are grown in an appropriate growth medium, such as LB (Luria- Bertani) medium, and this culture is spread onto agar, containing a suitable growth medium, such as LB medium with IPTG (isopropyl β-D-thiogalactopyranoside) and S-Gal™ (3,4-cyclohexenoesculetin-β-D-galactopyranoside). After growth, the plaques are picked for DNA isolation and sequencing to identify the skin care composition-resistant skin-binding peptide sequences. Alternatively, the eluted phage-peptides and the remaining bound phage-peptides may be amplified using a nucleic acid amplification method, such as the polymerase chain reaction (PCR). In that approach, PCR is carried out on the eluted phage-peptides and/or the remaining bound phage-peptides using the appropriate primers, as described by Janssen et al. in U.S. Patent Application Publication No. 2003/0152976, which is incorporated herein by reference.

In one embodiment, the eluted phage-peptides and the remaining bound phage-peptides are amplified by infecting a bacterial host cell, the amplified phage-peptides are contacted with a fresh skin sample, and the entire process described above is repeated one or more times to obtain a population that is enriched in skin care composition-resistant skin-binding phage-peptides. After the desired number of biopanning cycles, the amplified phage-peptide sequences are determined using standard DNA sequencing techniques that are well known in the art to identify the skin care composition-resistant skin-binding peptide sequences.

Production of Skin-Binding Peptides:

The skin-binding peptides of the present invention may be prepared using standard peptide synthesis methods, which are well known in the art (see for example stewart et al., *solid phase peptide synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding skin-binding peptides may be produced in heterologous host cells, particularly in the cells of microbial hosts.

Preferred heterologous host cells for expression of the binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include, but are not limited to, chromosomal, episomal and virus-derived vectors, e.g., vectors derived from bacterial plasmids, from bacteriophage, from transposons, from insertion elements, from yeast episoms, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct Chimeric genes for production of the any of the binding peptides of the present invention. These Chimeric genes could then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the Chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, IPL, IPR, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Peptide-Based Metal Oxide Sunscreen Agents:

The invention comprises a peptide-based metal oxide sunscreen agent. Additionally, the peptide-based metal oxide sunscreen agent is a reaction product of a skin-binding peptide and a metal oxide sunscreen agent. Additionally, the peptide-based metal oxide sunscreen agent can be formed by treating a metal oxide sunscreen agent with a skin-binding peptide. Additionally, the peptide-based metal oxide sunscreen agent is formed by coupling a skin-binding peptide (SBP) with a metal oxide sunscreen agent (SSA).

The skin-binding peptide part binds strongly to the skin, thus keeping the sunscreen agent attached to the skin for a long lasting sunscreen effect. The skin-binding peptides include, but are not limited to, skin-binding peptides selected by the screening methods described above, including the skin-binding peptide sequence disclosed by Huang et al. (copending and commonly owned U.S. patent application Ser. No. 10/935,642), given as SEQ ID NO:1. Additionally, any known skin-binding peptide may be used, including but not limited to, SEQ ID NO:2 and SEQ ID NOS:3-8, described by Janssen et al. In U.S. Patent Application Publication No. 2003/0152976 and by Janssen et al. In WO 04048399, respectively which are incorporated hereinby reference in their entireties.

Metal oxide sunscreen agents as herein defined include, but are not limited to titanium dioxide, zinc oxide, cerium oxide and iron oxides.

The peptide-based metal oxide sunscreen agents are prepared by covalently attaching a skin-binding peptide to the metal oxide sunscreen agent either directly or via a spacer. Any known peptide or protein conjugation chemistry may be used to form the peptide-based metal oxide sunscreen agent of the present invention. Conjugation chemistries are well-known in the art (see for example, Hermanson, *Bioconjugate Techniques*, Academic Press, New York (1996)). Suitable coupling agents include, but are not limited to, carbodiimide coupling agents, diacid chlorides, diisocyanates and other difunctional coupling reagents that are reactive toward terminal amine and/or carboxylic acid terminal groups on the peptides and to hydroxy groups or other groups on the metal oxide, specifically the alumina and/or silica of the treated surface of the metal oxide. The preferred coupling agents are carbodiimide coupling agents, such as 1-ethyl-3-(3-dimethylaminopropyl)-carbodiimide (EDC) and N,N'-dicyclohexyl-carbodiimide (DCC), which may be used to activate carboxylic acid groups for coupling to alcohol, and amine groups.

Additionally, it may be necessary to protect reactive amine or carboxylic acid groups on the peptide to produce the desired structure for the peptide-based metal oxide sunscreen agent. The use of protecting groups for amino acids, such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, or aldehyde groups, on the sunscreen agent for coupling to the skin-binding peptide. These modifications may be done using routine chemistry such as oxidation, reduction and the like, which is well known in the art.

It may also be desirable to couple the skin-binding peptide to the metal oxide sunscreen agent via a spacer. The spacer serves to separate the sunscreen agent from the peptide to ensure that the agent does not interfere with the binding of the peptide to the skin. The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The spacer may be covalently attached to the peptide and the sunscreen agent using any of the coupling chemistries described above. In order to facilitate incorporation of the spacer, a bifunctional cross-linking agent that contains a spacer and reactive groups at both ends for coupling to the peptide and the sunscreen agent may be used. Suitable bifunctional cross-linking agents are well known in the art and include, but are not limited to diamines, such a as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of heterobifunctional cross-linking agents include, but are not limited to compounds having the following structure:

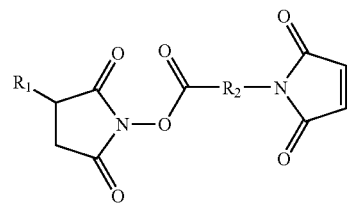

where: $R_1$ is H or a substituent group such as —$SO_3Na$, —$NO_2$, or —Br; and $R_2$ is a spacer such as —$CH_2CH_2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N-hydroxysuccinimide ester group of these reagents reacts with amine or alcohol groups on the conditioner, while the maleimide group reacts with thiol groups present on the peptide. A thiol group may be incorporated into the peptide by adding a cysteine group to at least one end of the binding peptide sequence. Several spacer amino acid residues, such as glycine, may be incorporated between the binding peptide sequence and the terminal cysteine to separate the reacting thiol group from the binding sequence.

Additionally, the spacer may be a peptide composed of any amino acid and mixtures thereof. The preferred peptide spacers are composed of the amino acids glycine, alanine, and serine, and mixtures thereof. In addition, the peptide spacer may contain a specific enzyme cleavage site, such as the protease Caspase 3 site, given by SEQ ID NO:2, which allows for the enzymatic removal of the sunscreen agent from the skin. The peptide spacer may be from 1 to about 50 amino acids, preferably from 1 to about 20 amino acids in length. These peptide spacers may be linked to the binding peptide sequence by any method know in the art. For example, the entire binding peptide-peptide spacer-diblock may be prepared using the standard peptide synthesis methods described supra. In addition, the binding peptide and peptide spacer blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid terminal groups on the peptides. Alternatively, the entire binding peptide-peptide spacer-diblock may be prepared using the recombinant DNA and molecular cloning techniques described supra. The spacer may also be a combination of a peptide spacer and an organic spacer molecule, which may be prepared using the methods described above.

It may also be desirable to have multiple skin-binding peptides attached to the metal oxide sunscreen agent to enhance the interaction between the peptide-based metal oxide sunscreen and the skin. Either multiple copies of the same skin-binding peptide or a combination of different skin-binding peptides may be used. In the case of large metal oxide particles and/or agglomerates, a large number of skin-binding peptides, i.e., up to about 1,000, may be attached to the sunscreen agent. A smaller number of skin-binding peptides can be attached to the smaller sunscreen nanoparticles, i.e., up to about 50. Therefore, in one embodiment of the present invention, the peptide-based metal oxide sunscreen agents are diblock compositions consisting of a skin care composition-resistant skin-binding peptide (SBP) and a metal oxide sunscreen agent (SSA), having the general structure $(SBP)_n$-SSA, where n ranges from 1 to about 1,000, preferably from 1 to about 50.

In another embodiment, the peptide-based metal oxide sunscreen contains a spacer (S) separating the skin care composition-resistant skin-binding peptide from the sunscreen agent, as described above. Multiple copies of the skin-binding peptide may be attached to a single spacer molecule. In this embodiment, the peptide-based metal oxide sunscreen agents are triblock compositions consisting of a skin care composition-resistant skin-binding peptide, a spacer, and a sunscreen agent, having the general structure $[(SBP)_m\text{-}S]_n$-SSA, where n ranges from 1 to about 1,000, preferably n is 1 to about 50, and m ranges from 1 to about 50, preferably m is 1 to about 10.

It should be understood that as used herein, SBP is a generic designation and is not meant to refer to a single skin-binding peptide sequence. Where n or m as used above, are greater than 1, it is well within the scope of the invention to provide for the situation where a series of skin-binding peptides of different sequences may form a part of the composition.

Sunscreen Formulation

The sunscreen formulation of this invention typically will contain an amount of peptide-based metal oxide sunscreen agent ranging from upto about 25 wt. %, typically from about 2 wt. % to up to about 10 wt. %, even more preferably upto 8 wt. %, based on the total weight of the formulation, the amount depending upon the desired sun protection factor (SPF) of the formulation.

The balance of the sunscreen formulation will be made up of the fluid vehicle and any other additives. Typically the fluid vehicle comprises water and other solvents which can include, without limitation, mineral oils and fatty alcohols.

The sunscreen formulations are usually an emulsion and the oil phase of the emulsion typically contains the UV active ingredients such as the metal oxide of this invention. Sunscreen formulations typically contain in addition to water, emollients, humectants, thickeners, UV actives, chelating agents, emulsifiers, suspending agents (typically if using particulate UV actives), waterproofers, film forming agents and preservatives.

Specific examples of preservatives include parabens. Specific examples of emollients include octyl palmitate, cetearyl alcohol, and dimethicone. Specific examples of humectants include propylene glycol, glycerin, and butylene glycol. Specific examples of thickeners include xanthan gum, magnesium aluminum silicate, cellulose gum, and hydrogenated castor oil. Specific examples of chelating agents include disodium ethylene diaminetetraacetic acid (EDTA) and tetrasodium EDTA. Specific examples of UV actives include ethylhexyl methoxycinnamate, octocrylene, and titanium dioxide. Specific examples of emulsifiers include glyceryl stearate, polyethyleneglycol-100 stearate, and ceteareth-20. Specific examples of suspending agents include diethanolamine-oleth-3-phosphate and neopentyl glycol dioctanoate. Specific examples of waterproofers include C30-38 olefin/isopropyl maleate/MA copolymer. Specific examples of film forming agents include hydroxyethyl cellulose and sodium carbomer.

Numerous means are available for preparing dispersions of titanium dioxide nanoparticles containing dispersants. Intense mixing, such as milling and grinding may be needed, for example, to break down agglomerates into smaller particles. To facilitate use by the customer, producers of titanium dioxide nanoparticles may prepare and provide dispersions of the particles in a fluid medium which are easier to incorporate into formulations.

The sunscreen formulation may also include typical sunscreen active ingredients for additional sunscreening capability. Typical sunscreen active ingredients are well-known. Specific examples include aminobenzoic acid (PABA), avobenzone, cinoxate, dioxybenzone, homosalate, methyl anthranilate, octocrylene, octyl methoxycinnamate, octyl salicylate, oxybenzone, padimate O, phenylbenzimidazole, sulisobenzone, trolamine salicylate. In addition the final formulation can contain a combination of metal oxide sunscreen agents such as combination of titanium dioxide and zinc oxide.

Methods for Treating Skin

In another embodiment, methods are provided for treating the skin or hair of an animal body, specifically a mammal body, even more specifically a human body, with the sunscreen formulation of the present disclosure. Methods well known to those skilled in the art of sunscreen formulating with particulate UV active ingredients can be used to incorporate peptide-based metal oxide sunscreen agents into sunscreens. The sunscreen formulation is prepared by mixing the peptide-based metal oxide sunscreen agent and the fluid vehicle together with any additional additives. The peptide-based metal oxide sunscreen agent can be added to the fluid vehicle at a temperature of about 60° to about 90° C., preferably about 70° to about 85° C. by any convenient means such as a homogenizer.

The present invention also comprises a method for forming a protective film of the sunscreen formulation on the hair or skin of the body by applying one of the compositions described above comprising an effective amount of a peptide-based metal oxide sunscreen agent to the hair or skin and allowing the formation of the protective film. The compositions of the present disclosure may be applied to the skin or hair by various means, including, but not limited to, spraying, brushing, and applying by hand. The sunscreen formulation can be left in contact with the skin or hair for a period of time sufficient to form the protective film, preferably for at least about 0.1 to 60 min.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Test Methods

Vitamin C Yellowing Test for Chemical Stability:

A standard solution of 6.25% ascorbic acid palmitate (L-ascorbic acid 6-palmitate, 99%, CAS #137-66-6, available commercially from Alfa Aesar) in octyl palmitate (hexadecanoic acid 2-ethylhexyl ester, CAS #29806-73-3, available under the name "Ceraphyl" by VanDyk) is prepared. Using a spatula and glass plate or Hoover Muller Model M5, 1.9+0.05 ml of the solution is thoroughly mixed with 0.4+0.01 g sample of titanium dioxide to be tested. The mixture is drawn down onto a white lacquered 3"×5" card using a 6 mil Bird film applicator to form the test film. The color (L*a*b*) of the test film is measured using a hand-held spectrocolorimeter, such as Byk-Gardner Model CB-6805 which is warmed-up prior to taking the color reading, calibrated and set up to use D65/10 degree (illuminant/observer). In the same manner as the test film, a blank film is prepared using neat octyl palmitate and ultrafine titanium dioxide. The color of the blank film is measured in the same way as the color of the test film. The delta b* value is determined by comparing the color of the test and blank films. The delta b* value is a measure of chemical activity.

UPA Particle Size Distribution

The MICROTRAC ULTRAFINE PARTICLE ANALYZER (UPA) (a trademark of Leeds and Northrup, North Wales, Pa.) uses the principle of dynamic light scattering to measure the particle size distribution of particles in liquid suspension. Leeds and Northrup, North Wales, Pa. manufacture the instrument. The measured size range is 0.003 μm to 6 μm (3 nm to 6000 nm). Use 2.55 for the refractive index of $TiO_2$ when setting up the UPA analysis. The dry particle sample needs to be prepared into a liquid dispersion to carry out the measurement. An example procedure is as follow:

(1) Weigh out 0.08 g dry powder.

(2) Add 79.92 g 0.1% tetra sodium pyrophosphate (TSPP) solution in water to make a 0.1 wt. % suspension.

(3) Sonify the suspension for 10 minutes using an ultrasonic probe. The suspension should be cooled in a water-jacketed beaker during sonication.

(4) When sonication is complete, draw an aliquot for analysis.

Note, hydrophobic particles must first be wetted with a few drops of ethanol before adding into solution of TSPP.

The results of these tests were reported below for each of the examples.

Example 1

In a half gallon plastic jug containing 100 g titanium dioxide nanoparticles made by RF plasma oxidation according to U.S. 2002/0155059A1, 800 mls. total volume deionized polished water was added and the mixture was stirred. The titanium dioxide nanoparticles starting material had a mean particle size of 90 nm, 10 wt % of particles less than 50 nm in size, and 90% of particles less than 150 nm in size as measured by the Microtrac UPA dynamic light scattering instrument. The mixture was sonicated for 10 minutes at a power of 7 and screened through a 325 mesh sieve. The screened mixture was added to a 2000 ml stainless steel beaker equipped with an electric stirrer, temperature probe and pH probe. The mixture was rapidly stirred using a propeller blade.

The initial pH was 1. The mixture was heated to 60° C. and the pH was adjusted to 7.1 with 50% NaOH solution (8.2 g). Then 9.0 g sodium aluminate (27.8 wt % alumina) was added. The pH was 10.8. The mixture was stirred for 15 minutes.

The mixture was heated to 92° C. The pH was 10.0. Then 1.6 g 50% citric acid solution was added. The pH after citric acid addition was 8.8. The pH was adjusted to 10.7 with 50% NaOH solution. Then 21.5 g sodium silicate (27 wt % silica) was added with strong stirring. The pH was 10.7. Over about 15 minutes concentrated (38%) hydrochloric acid solution was added to reduce the pH to 7 (17.7 g HCl). The mixture was stirred for 45 minutes at 92-95° C. The heat was stopped and the pH was reduced to the range of 6-8 with concentrated (38% HCl) (13.5 g) while adding 18.0 g sodium aluminate drop-wise over 15 minutes. The mixture was stirred for 20 minutes while maintaining a pH of 7. At the end of 20 minutes the temperature was 60. The pH was adjusted to 6.0±0.3 with concentrated (38%) HCl. The mixture was stirred again for 5 minutes. The final mixture was filtered, washed with deionized polished water to <143 mhos/cm conductance (~3 liters water, 106 micro mhos/cm). The mixture was vacuum dried for about 30 minutes to form a cake then ethanol was added to cover the cake for about 15 minutes. The cake was then vacuum dried again for about 30 minutes. The cake was dried in a 125° C. oven on a tray overnight. The dry particles were ground and sieved through a 35 mesh screen and dried again.

Measured $SiO_2$: 3.9%

Measured $Al_2O_3$: 5.7%

Example 2

The following materials were added to a 1000 ml plastic beaker: 50.00 g Degussa P25 titanium and 400 ml deionized polished water. The mixture was stirred then sonicated for 3 minutes at a power of 7. The mixture was then poured into a 600 ml stainless steel beaker equipped with an electric stirrer, temperature probe and pH probe. The mixture was agitated using a propeller blade. The initial pH of the mixture was 3.3. The mixture was heated to about 95° C. and 0.8 g citric acid 50% solution was added. The pH was 2.7. The pH was adjusted with 10% NaOH to a range of 9-9.5 by adding 3.8 g 50% NaOH solution. The neutral pH was maintained by adding 8.1 g concentrated (38%) HCl while adding 10.75 g sodium silicate drop wise over 14 minutes. The mixture was heated at 95° C. for one hour at pH 9.5 with stirring at about 2600 rpm. The pH was lowered to 7 by adding 8.1 g concentrated (38%) HCl while 9 g sodium aluminate was added drop wise over 10 minutes. The heat was turned off and the mixture was stirred for 20 minutes at pH of 7. The temperature after 20 minutes was 75.5° C. The pH was adjusted to 6.0+0.3 with HCl and stirred for 5 minutes.

The mixture was filtered, washed and dried and the dry particles were formed as in Example 1.
Measured $SiO_2$: 4.4%
Measured $Al_2O_3$: 3.2%

Example 3

The treatment was performed as in Example 1 except no sodium aluminate was added prior to the addition of sodium silicate.
Measured $SiO_2$: 4.1%
Measured $Al_2O_3$: 4.4%

Example 4

The aqueous mixture of titanium dioxide was prepared, stirred then solicated and pH adjusted as in Example 1. The initial pH was 1.5. The mixture was heated to 60° C. and the pH was adjusted to 7.3 with 50% NaOH solution (8.2 g). Then 9.0 g sodium aluminate (27.8 wt % alumina) was added. The pH was 11.4. The mixture was stirred for 15 minutes.

The mixture was heated to 92° C. The pH was 10.9. Then 4.8 g 50% citric acid solution was added. The pH after citric acid addition was 9.7. The pH was adjusted to 10.9 with 50% NaOH solution. Then 64.5 g sodium silicate (27 wt % silica) was added with strong stirring. The pH was 11.0. Over about 15 minutes concentrated (38%) hydrochloric acid solution was added to reduce the pH to 7 (23.5 g.HCl). The mixture was stirred for 45 minutes at 2-95° C. The heat was stopped and the pH was reduced to the range of 6-8 with concentrated (38% HCl)(37.4 g) while adding 54.0 g sodium aluminate drop-wise over 13 minutes. The mixture was stirred for 20 minutes while maintaining a pH of 7. At the end of 20 minutes the temperature was 44° C. The pH was adjusted to 6.0+0.3 with concentrated (38%) HCl The mixture was stirred again for 5 minutes. The final mixture was filtered, washed with deionized polished water to <143 mhos/cm conductance (~3 liters water, 100 micro mhos/cm). The mixture was vacuum dried for about 30 minutes to form a cake then ethanol was added to cover the cake for about 15 minutes. The cake was then vacuum dried again for about 30 minutes. The cake was dried in a 125° C. oven on a tray overnight. The dry particles were ground and sieved through a 35 mesh screen and dried again.
Measured $SiO_2$: 10.1%
Measured $Al_2O_3$: 14.5%

Example 5

The aqueous mixture of titanium dioxide was prepared, stirred, sonicated and pH adjusted as in Example 1. It was then heated to 60° C. and stirred for 15 minutes, then filtered, washed, and dried as in Example 1.
Measured $SiO_2$: 0.0%
Measured $Al_2O_3$: 0.0%

Example 6

The following materials were added to a 1000 ml plastic beaker: 50.00 g Degussa P25 titanium dioxide and 400 ml deionized polished water. The mixture was stirred then sonicated for 3 minutes at a power of 7. The mixture was then agitated with an electric stirrer motor and heated to 92° C. The initial pH was 3.2. The pH was adjusted to 9.2 using 1.4 g 10% NaOH. The pH of the mixture was maintained in a range of 9-10 using HCl (18%, 10.3 g, 50% dilute) while 18.5 g sodium silicate solution (27 wt. % $SiO_2$) was added drop wise over 8 minutes. The mixture was heated for one hour.

The mixture was filtered, washed and dried as described in Example 1 and the particles were ground and sieved through a mesh screen and dried again.
Measured $SiO_2$: 8.33%

Example 7

The aqueous mixture of titanium dioxide was prepared, stirred then sonicated as described in Example 2. The initial pH was in the range of 3.3-3.6. The mixture was heated to about 91° C. The pH was adjusted to 9.4 using 1.24 g 10% NaOH. The pH of the mixture was maintained in a range of 9-9.5 using HCl (18%, 20.63 g, 50% dilute) while adding 37.04 g sodium silicate solution (27 wt. % $SiO_2$) drop wise over about 40 minutes. The mixture was heated to 91-97° C. for one hour at pH of 9.3.with mixing at about 2700 rpm.

The mixture was filtered, washed and dried as described in Example 1 and the particles were ground and sieved through a 100 mesh screen and dried again.
Measured $SiO_2$: 13.0%

Example 8

The aqueous mixture of titanium dioxide was prepared, stirred then sonicated as described in Example 2. The initial pH was in the range of 3.4-3.8. The mixture was heated to 92° C. The pH was adjusted to 9.2 using 1.1 g 10% NaOH. The pH of the mixture was maintained in a range of 9-9.5 using HCl (38%, 39.20 g, 50% dilute) while adding 55.56 g sodium silicate solution (27 wt. % $SiO_2$) drop wise over about 27 minutes. The mixture was heated to 94° C. for one hour at pH of 9.4.with mixing at about 3500 rpm.

The mixture was filtered, washed and dried as described in Example 1 and the particles were ground and sieved through a 100 mesh screen and dried again.
Measured $SiO_2$: 20.0%

Example 9

The aqueous mixture of titanium dioxide was prepared, stirred then sonicated as described in Example 2. The initial pH was in the range of 3.0-3.1. The mixture was heated to 92° C. The pH was adjusted to 9.1-9.5 using about 1.6 g 10% NaOH and maintained at that pH. The mixture was heated to 90-98° C. for one hour at pH of 9.5. The mixture was filtered, washed and dried as described in Example 1 but it was noted that filtering and washing was slower than Examples made with sodium silicate. The dried material had a tan color. The particles were ground and sieved through a 100 mesh screen and dried again.
Measured $SiO_2$=0%
Measured $Al_2O_3$=0%

Example 10

The aqueous mixture of titanium dioxide was prepared, stirred then sonicated and pH adjusted as in Example 1. The mixture was heated to 60° C.

Then 27.0 g sodium aluminate (27.8 wt % alumina) was added while keeping the pH in the range of 6-8 using 19.5 g of concentrated (38%) HCl. The mixture was then stirred for 20 minutes maintaining the pH and temperature.

The material was then filtered, washed, dried, and crushed as in Example 1.

Measured $Al_2O_3$=4.7%

TABLE 1

| Example | % $SiO_2$ | % $Al_2O_3$ | Delta b*[1] | $PSD^2$ |
|---|---|---|---|---|
| 1 | 3.9 | 5.7 | 1.7 | 54 |
| 2 | 4.4 | 3.2 | 3.5 | 50 |
| 3 | 4.1 | 4.4 | 5.4 | 65 |
| 4 | 10.1 | 14.5 | 1.0 | 61 |
| 5 | 0 | 0 | 27 | 13 |
| 6 | 8.3 | 0 | 17.6 | 45 |
| 7 | 13.0 | 0 | 12.6 | 61 |
| 8 | 20.0 | 0 | 4.3 | 85 |
| 9 | 0 | 0 | 25 | 32 |
| 10 | 0 | 4.7 | 23 | — |

[1]As determined by the Vitamin C Yellowing Test
[2]As determined by the MICROTRAC UPA The delta b* (an indication of chemical activity) values of Examples 6, 7 and 8 show that increasing the % silica lowers the delta b* values which indicates that higher levels of silica will lead to a more chemically stable product. However, as the silica content increases the particles have a greater tendency to form agglomerates, as indicated by the PSD values. Example 2 shows that titanium dioxide particles having silica and alumina coatings have a low delta b* value indicating good chemical stability especially in comparison to untreated material (Example 5) and, in addition, the agglomeration is substantially reduced, as indicated by the PSD values. Thus, silica and alumina coated titanium dioxide nanoparticles having low surface treatment levels have chemical stability properties which are as good as, if not better than, titanium dioxide particles that contain high silica levels. Examples 1, 2, and 3 show that this treatment can also be applied to a titanium dioxide nanoparticles formed by different processes with good effectiveness and produce chemically stable particles, especially compared to the untreated material (Example 5), that have reduced agglomeration compared to silica only treated particles (Example 8).

Example 11

The purpose of this Example is to describe the preferred embodiments for identification of phage peptides that have a high binding affinity to skin. The modified biopanning method as described by Huang et al. (copending and commonly owned U.S. patent application Ser. No. 10/935,642) was used to identify the high affinity, skin-binding phage-peptide clones. Pig skin served as a model for human skin in the process and was prepared by methods cited in above reference. A total of 28 single black phage plaques were picked randomly for DNA isolation and sequencing analysis and one repeated dine was identified. The amino acid sequence of this phage peptide, which appeared 9 times out of the 28 sequences was TPFHSPENAPGS, given as SEQ ID NO: 1. SEQ ID NO: 2 represents the Caspase 3 Cleavage Site, LESGDEVD.

Example 12—Prophetic

The purpose of this Example is to describe a way to prepare a metal oxide sunscreen agent by covalently linking the skin-binding peptide, given as SEQ ID NO:1 to the surface of a titanium dioxide particle, prepared as described in Examples 1-10. The surface of the titanium dioxide is coated with alumina and silica to reduce photoactivity. These coating provide good surface chemistry to covalently link to the specific skin-binding peptide.

The titanium dioxide (87 mg), peptide (80 mg) and dicyclohexyl carboiimide (22 mg) could be added to 3 mL of tetrahydrofuran (THF). A solution of dimethyl aminopyridine (17 µL) in several drops of THF was added dropwise to this mixture with stirring. The resulting suspension could be heated to 40° C. for 6 h with stirring, followed by stirring overnight at room temperature. Trifluoroacetic acid (0.6 mL) could be added to the product and the mixture could be stirred for another 6 h. Then, 5 mL of deionized water could be added to the reaction mixture. The mixture could then be centrifuged at 3,5000 rpm for 2 min and the supernatant decanted. The solid remaining in the centrifuge tube could be washed with deionized water and centrifuged again. This washing could be repeated until the pH of the supernatant reached approximately 6.0.

Example 13—Prophetic

The purpose of the Example is to describe a method of preparing sunscreen containing a peptide-based metal oxide sunscreen agent. It is speculated that a long-lasting, waterproof sunscreen could be preparing by first heating cyclopentasiloxane (10 g) and cyclomethicone (10 g) to about 75° C. Approximately 5 wt %, based on final formulation, of the peptide-based metal oxide sunscreen agent, prepared as described in Example 12, could be stirred into the mixture until thoroughly mixed. Water (60 g) could then be slowly added to the mixture and then be milled on homogenizer for about 5 minutes and then allowed to cool.

The description of illustrative and preferred embodiments of the present disclosure is not intended to limit the scope of the invention. Various modifications, alternative constructions and equivalents may be employed without departing from the true spirit and scope of the appended claims.

What is claimed is:

1. A sunscreen formulation comprising:
   (a) a peptide-based metal oxide sunscreen agent having a general structure selected from the group consisting of:
      (i) $(SBP)_n$-SSA, and
      (ii) $[(SBP)_m$-S$]_n$- SSA,
      wherein:
         (A) SBP is a skin-binding peptide,
         (B) S is a spacer having first and second ends,
         (C) SSA is a metal oxide sunscreen agent,
         (D) n ranges from 1 to about 1,000, and
         (E) m ranges from 1 to about 50; and
   (b) a fluid vehicle.

2. The sunscreen formulation of claim 1 wherein the metal oxide of the peptide-based metal oxide sunscreen agent is selected from the group consisting of titanium dioxide, zinc oxide, cerium oxide and iron oxide and combinations thereof.

3. The sunscreen formulation of claim 1 wherein the metal oxide of the peptide-based metal oxide sunscreen agent comprises metal oxide nanoparticles selected from the group consisting of titanium dioxide, zinc oxide, cerium oxide and iron oxide and combinations thereof.

4. The sunscreen formulation of claim 1 wherein the metal oxide of the peptide-based metal oxide sunscreen agent comprises titanium dioxide nanoparticles.

5. The sunscreen formulation of claim 1 wherein the metal oxide of the peptide-based metal oxide sunscreen agent is treated with a source of silica or alumina or a combination thereof.

6. The sunscreen formulation of claim 5 wherein the metal oxide of the peptide-based metal oxide sunscreen agent is treated in the presence of a densifying agent.

7. The sunscreen formulation of claim 6 wherein the densifying agent is citric acid.

8. The sunscreen formulation of claim 7 wherein the metal oxide of the peptide-based metal oxide sunscreen agent is titanium dioxide nanoparticles.

9. The sunscreen formulation of claim 1 wherein the peptide-based metal oxide sunscreen agent comprises up to 25 wt % of the total weight of the sunscreen formulation.

10. The sunscreen formulation of claim 1 wherein n is 1 to about 50.

11. The sunscreen formulation of claim 1 wherein m is 1 to about 10.

12. The sunscreen formulation of claim 1 wherein the spacer comprises a protease caspase cleavage site having SEQ ID NO: 9.

13. The sunscreen formulation of claim 1 wherein the spacer is selected from alkyl chains, phenyl compounds, ethylene glycol, amides, and esters.

14. The sunscreen formulation of claim 1 wherein the spacer is hydrophilic and has a chain length from 1 to about 100 atoms.

15. The sunscreen formulation of claim 1 wherein the spacer is hydrophilic and has a chain length about 2 to about 30 atoms.

16. The sunscreen formulation of claim 1 wherein the spacer is selected from ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl, propyl, hexyl, steryl, cetyl, and palmitoyl alkyl chains.

17. The sunscreen formulation of claim 1 wherein the spacer is covalently attached to the SBP and SSA and comprises reactive groups.

18. The sunscreen formulation of claim 17 wherein the spacer and reactive groups comprise a bifunctional cross-linking agent.

19. The sunscreen formulation of claim 18 wherein the bifunctional cross-linking agent is selected from the group of diamines, dialdehydes, bis N-hydroxysuccinimide esters, diisocyanates, bis oxiranes, and dicarboxylic acids.

20. The sunscreen formulation of claim 18 wherein the reactive groups on each end of the spacer are different.

21. The sunscreen formulation of claim 18 wherein the crossliniking agent has the following structure:

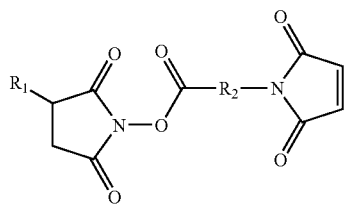

wherein $R_1$ is H or a substituent group selected from —$SO_3Na$, —$NO_2$, and —Br; and $R_2$ is a spacer comprising —$CH_2CH_2$ (ethyl), —$(CH_2)_3$ (propyl), or—$(CH_2)_3$ $C_6H_5$ (propyl phenyl).

22. The sunscreen formulation of claim 18 wherein the crossliniking agent is 3-maleimidopropionic acid N-hydroxysuccinimide ester.

23. A method for treating skin or hair comprising applying the sunscreen formulation of claim 1 to the skin or hair.

24. The sunscreen formulation of claim 1 wherein the metal oxide of the peptide-based metal oxide sunscreen agent is in a crystalline form having a crystal lattice and said crystal lattice is doped with an element which is different from the metal of the metal oxide to modify the color of the metal oxide.

25. The sunscreen formulation of claim 24 wherein the lattice is doped with iron or manganese.

26. The sunscreen formulation of claim 1 wherein the metal oxide of the peptide-based metal oxide sunscreen agent is in a crystalline form having a crystal lattice and said crystal lattice is doped with an element which is different from the metal oxide to decrease the photoactivity of the metal oxide.

27. The sunscreen formulation of claim 26 wherein the crystal lattice of the metal oxide is doped with manganese, iron, vanadium, or chromium.

28. The sunscreen formulation of claim 24 or 26 in which the element doped in the crystal lattice is present in an amount ranging from about 0.01% to about 5% based on the entire weight of the metal oxide.

29. The sunscreen formulation of claim 1 wherein the spacer is a peptide spacer comprising from 1 to about 50 amino acids.

30. The sunscreen formulation of claim 29 wherein the peptide spacer comprises amino acids selected from the group consisting of glycine, alanine, serine, and mixtures thereof.

* * * * *